(12) United States Patent
Moo-Young (10) Patent No.: US 6,767,902 B2
(45) Date of Patent: Jul. 27, 2004

(54) ANDROGEN AS A MALE CONTRACEPTIVE AND NON-CONTRACEPTIVE ANDROGEN REPLACEMENT

(75) Inventor: Alfred J. Moo-Young, Hastings-On-Hudson, NY (US)

(73) Assignee: The Population Council, Inc., New York, NY (US)

( * ) Notice: Subject to any disclaimer, the term of this patent is extended or adjusted under 35 U.S.C. 154(b) by 0 days.

(21) Appl. No.: 09/154,283

(22) Filed: Sep. 16, 1998

(65) Prior Publication Data

US 2002/0193359 A1 Dec. 19, 2002

Related U.S. Application Data

(60) Provisional application No. 60/059,300, filed on Sep. 17, 1997, and provisional application No. 60/062,962, filed on Oct. 10, 1997.

(51) Int. Cl.$^7$ .................. A61K 31/568; A61P 15/16
(52) U.S. Cl. .................. 514/178; 514/841; 514/842
(58) Field of Search .................. 514/178, 841, 514/842

(56) References Cited

U.S. PATENT DOCUMENTS

| | | | |
|---|---|---|---|
| 4,177,267 A | 12/1979 | Herschler | 424/238 |
| 4,573,996 A | 3/1986 | Kwiatek et al. | 604/897 |
| 4,615,697 A | 10/1986 | Robinson | 604/890 |
| 4,788,218 A | * 11/1988 | Tanabe et al. | |
| 5,332,576 A | 7/1994 | Mantelle | 424/443 |
| 5,342,834 A | 8/1994 | Bardin et al. | 514/178 |
| 5,503,804 A | 4/1996 | Fujishita et al. | 422/109 |
| 5,662,926 A | 9/1997 | Wick et al. | 424/448 |
| 5,676,969 A | 10/1997 | Wick et al. | 424/448 |
| 5,683,711 A | 11/1997 | Fischer et al. | 424/449 |
| 5,733,565 A | 3/1998 | Moo-Young et al. | |

OTHER PUBLICATIONS

Cas Ads 127:90667 Surisaari et al 1997.*
Satas' Handbook of Pressure Sensitive Adhesive Technology "Acrylic Adhesives," $2^{nd}$ Ed., p. 396–456 (1989).
Kumar et al., "The Biological Activity of 7 Alpha–Methyl–19–Nortestosterone Is Not Amplified In Male Reproduction," WHO Laboratory Manual for the Examination of Human Semen and Sperm—Cervical Mucus Interaction, 3d. Ed. Cambridge Univ. Press 1992.
Sobieski et al., Silicone Pressure Sensitive Adhesives, Handbook of Pressure Sensitive Adhesive Technology, $2^{nd}$ Ed., p. 508–517 (1989).
Sundaram, Kalyan et al.: "7–alpha–methyl–19–nortestosterone (MENT): an ideal androgen for replacement therapy," Pharmacology, Biology, and Clinical Applications of Androgens: Current Status and Future Prospects, Proceedings of the International Androgen Workshop, 2nd, Long Beach, California, Feb. 17–20, 1995 (1996), Meeting Date 1995, 493–497, Editor: Bhasin, S. XP–001105252.
Sundaram et al., "7 Alpha–Methyl–Nortestosterone (MENT): The Optimal Androgen For Male Contraception" Annals of Medicine, (1993), 25, 199–205.

* cited by examiner

*Primary Examiner*—Edward J. Webman
(74) *Attorney, Agent, or Firm*—Lerner, David, Littenberg, Krumholz & Mentlik, LLP (57) ABSTRACT

The present invention relates to methods of providing male contraception using a specified androgen without the need of a separate sterilizing agent. The invention also describes methods for non-contraceptive androgen replacement and devices useful for carrying out both processes.

20 Claims, 7 Drawing Sheets

ANDROGEN AS A MALE CONTRACEPTIVE AND NON-CONTRACEPTIVE ANDROGEN REPLACEMENT

CROSS-REFERENCE TO RELATED APPLICATIONS

The present application claims benefit of U.S. Provisional Patent Application Nos. 60/059,300 and 60/062,962, filed Sep. 17, 1997, and Oct. 10, 1997, respectively, the disclosures of which are hereby incorporated by reference herein.

Financial support for the invention described herein was received from the U.S. Agency for International Development under Cooperative Agreement No. DPE-3050-A-00-80S9-00. Therefore, the U.S. Government may have certain rights in the invention.

FIELD OF THE INVENTION

The present invention relates to the fields of medicine and pharmaceutical science in providing androgen replacement methods of male contraception and devices useful in accordance with those methods.

BACKGROUND OF THE INVENTION

Male contraception has been enigmatic. Mechanical devices offer reduced sensation and inconvenience. While they may be effective in reducing the transmission of sexually transmitted diseases, they may also be a source of friction in a relationship. Moreover, such contraceptive methods are not without a significant incidence of failure.

For these and other reasons, chemical methods, such as birth control pills for women, have been a long sought after objective. However, chemical protocols for men have been plagued by their own problems. For example, the continuous administration of luteinizing hormone releasing hormone (LHRH) and its analogs have been proposed as an effective way of suppressing spermatogenesis. This is accomplished by blocking gonadotropin secretion. Implants that deliver LHRH and its analogs therefore represent a potential male contraceptive. However, the loss of gonadotropins results in diminished secretion of testosterone which, amongst other things, provides a diminished libido and potential loss of sexual function. Therefore, along with the administration of LHRH, or another sterilant, the art recognizes the need for the co-administration of an androgen. See U.S. Pat. No. 5,733,565. An androgen, often testosterone, is supplied to help bolster the body's testosterone level and sustain normal sexual function. This sort of androgen supplementation, however, brings with it many problems of its own. Testosterone is expensive and relatively large quantities need to be administrated, usually by injection, on a daily basis. Testosterone is also 5α-reduced to DHT (dihydrotestosterone) which is itself a very potent agent. It can over-stimulate prostate growth, potentially leading to complications such as BPH (benign prostate hypoplasia).

In view of the foregoing, there remains a need for an effective method of male contraception with a minimum of health risks and further complications. That need is satisfied by the present invention.

SUMMARY OF THE INVENTION

The present invention is based on, amongst other things, the discovery that an androgen can be used alone as an effective contraceptive, not merely as an androgen supplement. By using an androgen as a contraceptive, one is able to eliminate the need for combination therapies using androgens and sterilants simplifying contraception and lowering costs dramatically. Moreover, the androgens used in accordance with the present invention not only act as contraceptives, but also maintain male sexual function and desire, without the side effects and adversities realized by the administration of 5α-reducible androgens such as testosterone.

In accordance with a preferred embodiment, the present invention relates to methods of male contraception which include administering to a non-sterile male subject a predetermined amount of an androgen which is sufficient to render that male subject reversibly sterile. If the dosage forms used in the methods of the present invention are for daily dosing, then sufficient androgen must be provided for that day. If the dosage form is active over a plurality of days, then sufficient androgen must be provided for the entire period. Stated another way, the amount of androgen administered must be sufficient to render the subject sterile each day over the predetermined period of time.

The androgen, when provided in the amounts contemplated will result in blood levels of luteinizing hormone (LH) and follicle stimulating hormone (FSH) of 2.5 International units/liter ("IU/L") or less and blood levels of testosterone (T) of 10 nmol/L or less. Preferably, the androgen is a non 5α-reducible androgen, such as a 7α-modified androgen. More preferably, the androgen, when provided in the amounts contemplated, will result in blood levels of LH and FSH of 2.0 IU/L or less and blood levels of T of 4 nmol/L or less. Most preferably, the androgen when provided in the amounts contemplated, will result in blood levels of LH and FSH of 1.0 IU/L or less, and blood levels of T of 3 nmol/L or less. Assuming that the androgen used is MENT, a steady-state blood level of more than 1.0 nmol/liter ("nmol/L") should result. Preferably, blood levels of MENT of 1.5 nmol/L and even more preferably of 2 nmol/L or more will result.

If the goal is to provide contraception over a period of six months, then a sufficient amount of the androgen as described above must be supplied to the subject each day so as to ensure contraceptive efficacy each day for six months. That means that the blood levels should, at least generally, be within the specified limits for LH, FSH and testosterone as discussed above. Of course, day-to-day variation is to be expected based on the subject, the mode of administration, and the like. However, on balance, the subject should receive enough androgen, preferably each day, to ensure that over the six month period the subject is, for all practical purposes, incapable of reproduction.

Dosage forms which contain a sufficient quantity of the specified androgens are also contemplated. These dosage forms, unlike those that have gone before, will provide sufficient androgen to be contraceptively effective without also causing certain side effects such as, for example, overstimulating the prostate. The dosage forms contemplated include, without limitation, the androgen and a pharmaceutically acceptable carrier.

With the understanding that androgens can be used alone as a contraceptive also comes a new understanding of the use of androgens in androgen replacement therapy. There are certainly instances when one would wish to bolster or augment a subject's androgen level to provide a certain therapeutic effect, i.e., enhanced sexual drive, without also providing contraception. Therefore, the present invention also relates to methods of androgen replacement therapy which comprise the administration of androgen to a male subject in an amount which is sufficient to treat the subject's condition without being contraceptively effective. The androgen, when provided in the amounts contemplated in accordance with this aspect of the present invention, will result in blood levels of LH and FSH of greater than 2.5 IU/L and blood levels of testosterone of greater than 10 nmol/liter. Preferably, the androgen is a non-5α-reducible androgen such as a 7α-modified-androgen. This means that the amount of androgen provided is less than that necessary to provide effective contraception, yet sufficient to provide some level of other therapeutic effect. Dosage forms useful in accordance with this aspect of the invention are also contemplated.

BRIEF DESCRIPTION OF THE DRAWINGS

FIG. 1—is a graph of the steady-state blood levels of MENT in subjects with either one, two or four MENT Ac implants. Values shown are means ±SE. Data from three clinics are presented. FIG. 1a (Clinic 1), FIG. 1b (Clinic 2) and FIG. 1c (Clinic 3).

DETAILED DESCRIPTION OF THE PREFERRED EMBODIMENTS

Before discussing the invention in detail, some definitions are appropriate. A "male subject," in accordance with the present invention, is a male mammal. Preferably, however, a male subject is a human male. All dosages discussed herein relate to an "average" sized human male. However, dosages can be scaled accordingly, using known principals of pharmacy, to accommodate other species of mammal.

A "non-sterile" male subject is a male subject capable of producing a sufficient quantity of viable sperm which, under the right conditions, can lead to reproduction. A "sterile male" or "sterile male subject" is a male who does not produce sperm, does not produce sperm in sufficient quantity, or does not produce sufficient viable sperm so as to make reproduction difficult and preferably impossible. While a non-sterile man normally produces about 100 to 300 million sperm per milliliter of ejaculate, clinically sterile males generally produce less than about 3 million sperm per milliliter of ejaculate or less. While it is still possible, even at 3 million sperm per milliliter of ejaculate, to fertilize an egg; statistically speaking, the chances of that happening are greatly reduced. Indeed, this level has been acknowledged as "clinical sterility." See "W.H.O. Laboratory Manual for the Examination of Human Semen and Sperm—Cervical Mucus Interaction," 3d Ed. Cambridge Univ. Press, 1992.

It is a goal of one aspect of the present invention to provide reversible sterility. "Reversible," in the context of the present invention, means that once the methods of the present invention are discontinued, a male subject previously undergoing treatment will be returned to a condition which will permit reproduction under normal conditions. At the very least, the androgen will not present a continued obstacle to reproduction after therapy is discontinued. Reversible does not necessarily mean instantaneous. Full potency may not be restored for days or even weeks after treatment is discontinued.

"Androgen," in accordance with the present invention, is any natural or synthetic male sex hormone including analogs and salts thereof which are pharmaceutically acceptable and which, when administered in accordance with the present invention, provide contraceptive efficacy. Contraceptive efficacy in accordance with the present invention can be defined by the level of sperm produced as defined above in terms of sterility. However, preferably, contraceptive efficacy and sterility are defined herein by the blood levels of certain compounds normally found in the circulating blood of male subjects. The androgen, when provided in the amounts contemplated, will result in blood levels of LH and FSH of 2.5 IU/L or less and blood levels of testosterone of 10 nmol/liter or less. More preferably, the androgen, when provided in the amounts contemplated, will result in blood levels of LH and FSH of 2.0 IU/L or less and blood levels of testosterone of 5 nmol/liter or less and even more preferably blood levels of LH and FSH of 1.5 IU/L or less and blood levels of testosterone of 4 nmol/liter or less. Most preferably, the androgen, when provided in the amounts contemplated, will result in blood levels of LH and FSH of 1.0 IU/L or less and blood levels of testosterone of 3 nmol/liter or less.

Preferably, the androgen used is a non-5α-reducible androgen. Testosterone is excluded by this definition as it is a 5α-reducible androgen, and as such, can produce higher levels of adverse side effects than equivalent potencies of other androgens as described. Its use would also not lower serum testosterone levels. Non-5α-reducible androgens include, without limitation, 7α-modified-androgens. Examples of these include 7α-alkyl-androgens such as 7α-methyl-14-dehydro-19-nortestosterone (CDB-868B), 7α-methyl-17aβ-propionyloxy-D-homoestra-4, 16, dien-3-one (CDB 2322A) and 7α-methyl-19-nortestosterone (MENT) and their pharmaceutically acceptable salts. See Kumar et al., "The Biological Activity of 7α-Methyl-19-Nortestosterone Is Not Amplified in Male Reproductive Tract as is That of Testosterone," *Endocrinology*, Vol. 130, No. 6, pgs. 3677–3683 (1992). The preferred androgen is MENT, its acetate, MENT Ac and related compounds.

Other androgen compounds useful in the method of the invention are testosterone derivatives having a non-hydrogen substituent in the 6α or 7α position. As used in the application, the term testosterone derivatives encompasses compounds having the basic four ring structure of testosterone, optionally modified at the 3, 5, 9, 11, 17 or 19 positions. Examples of such compounds include:

7-α-methyl testosterone,
7-α-methyl-11β-hydroxytestosterone,
7-α,17-dimethyltestosterone,
7-α,17-dimethyl-11β-hydroxytestosterone,
7-α,17-dimethyl-19-nortestosterone,
7-α,17-dimethyl-11β-hydroxy-19-nortestosterone,
6-α-methyl testosterone,
6-α-methyl-19-nortestosterone,
6-α-methyl-11β-hydroxytestosterone,
6-α,17-dimethyltestosterone,
6-α,17-dimethyl-11β-hydroxytestosterone,
6-α,17-dimethyl-19-nortestosterone, and
6-α,17-dimethyl-11β-hydroxy-19-nortestosterone The 7α-methyl testosterone compounds for use in the invention can be prepared as described in U.S. Pat. No. 3,341,557 which is incorporated herein by reference. Synthesis of the other compound identified herein have also been described in the literature.

Figure 5:
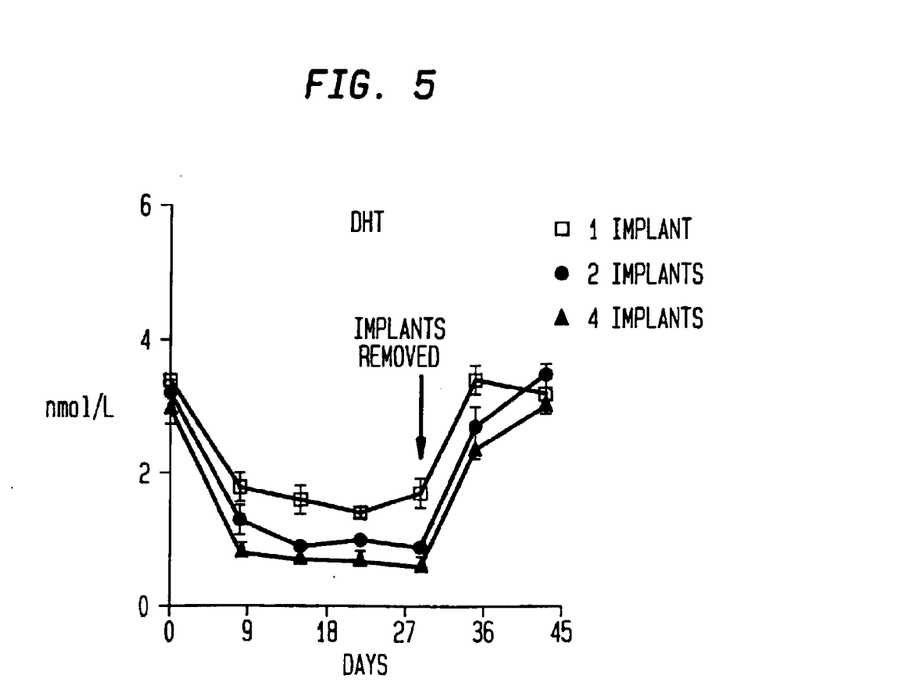
FIG. 5—is a graph of the effect of MENT Ac implants on serum levels of DHT. Values shown are means ±SE.

Preferably, the androgens used should have a minimum of side effects. One method of determining the degree of side effects exhibited by a particular androgen is by measuring its ability to stimulate the prostate. Compounds such as testosterone can overstimulate the prostate. MENT, however, stimulates the prostate to a much lower degree, particularly in the potency ranges contemplated as part of the present invention. Indeed, as shown in FIG. 5, levels of the metabolite DHT actually decreased along with the levels of LH FSH and testosterone since, by use of the present invention, the bodies production of testosterone is reduced.

The "predetermined amount" or "amount" of androgen as used in accordance with the present invention can vary widely, depending on a number of factors known to practitioners of the medical and pharmaceutical sciences. The predetermined amount can depend on factors such as the size, weight, hormone level and age of the subject, the subject's sperm count, the type of androgen used, the possibility of interactions with other therapies and the type of dosage form used. For example, more androgen may need to be administered to a subject transdermally to arrive at the appropriate blood level when compared to the IV administration of the same androgen. In addition, the properties of a salt form of an androgen may affect the transdermal qualities of a drug when compared to other forms of the same androgen.

Also important to a determination of the amount of androgen to be delivered each day is the objective. More androgen is needed for contraception than non-contraceptive androgen replacement. Because of the wide variation in these factors, factors which will vary from dosage form to dosage form, from androgen to androgen and from subject to subject, it is far more convenient to describe the amount of androgen useful in terms of the amount of a particular androgen which is necessary to produce certain levels of various chemicals in the subject, on average, each day of treatment. As previously discussed, when the objective is male contraception, the amount contemplated, will result in blood levels of LH and FSH of 2.5 IU/L or less and blood levels of testosterone of 10 nmol/liter or less. At these levels, on the average, a person has been provided with an amount of androgen necessary to provide a contraceptive effect each day, i.e., over a 24 hour period. If non-contraceptive androgen replacement is the object, then blood levels of LH, FSH, and testosterone should be higher than 2.5 IU/L and 10 nmol/liter respectively.

A "predetermined time" in accordance with the present invention is preferably at least a plurality of days and preferably, at least seven days. Even more preferably, the amount of androgen administered will be sufficient to provide contraceptive efficacy each day over a 30 day period of time and most preferably over at least about 180 days. Thus, when a device is to be used to provide contraception over a predetermined time of about 180 days, for example, the device must comprise sufficient androgen to provide the desired blood levels of LH, FSH and testosterone each day over that period of time. Of course, it may take 30 or more days before the administration of androgen at the levels described herein is contraceptively effective.

Figure 1A:
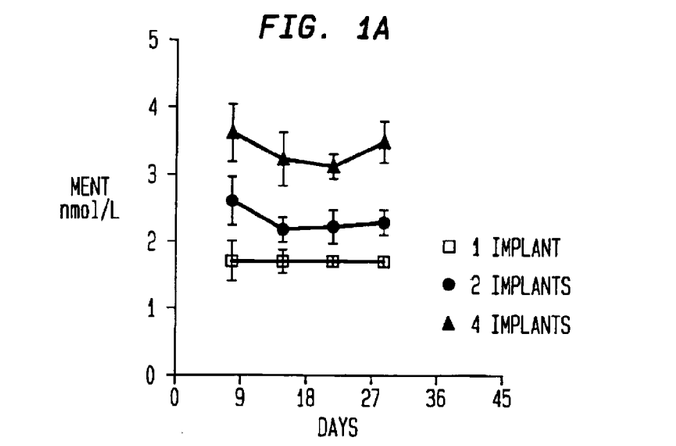
Figure 1B:
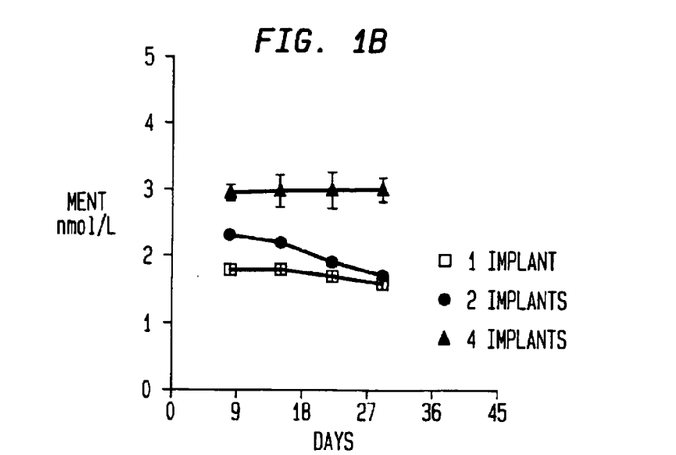
Figure 1C:
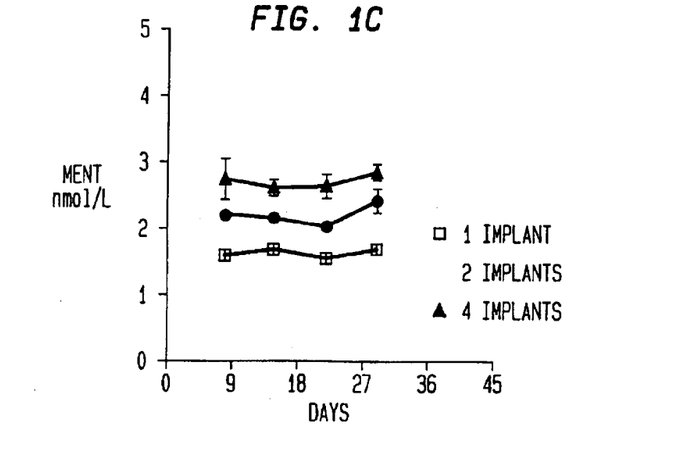
Figure 6:
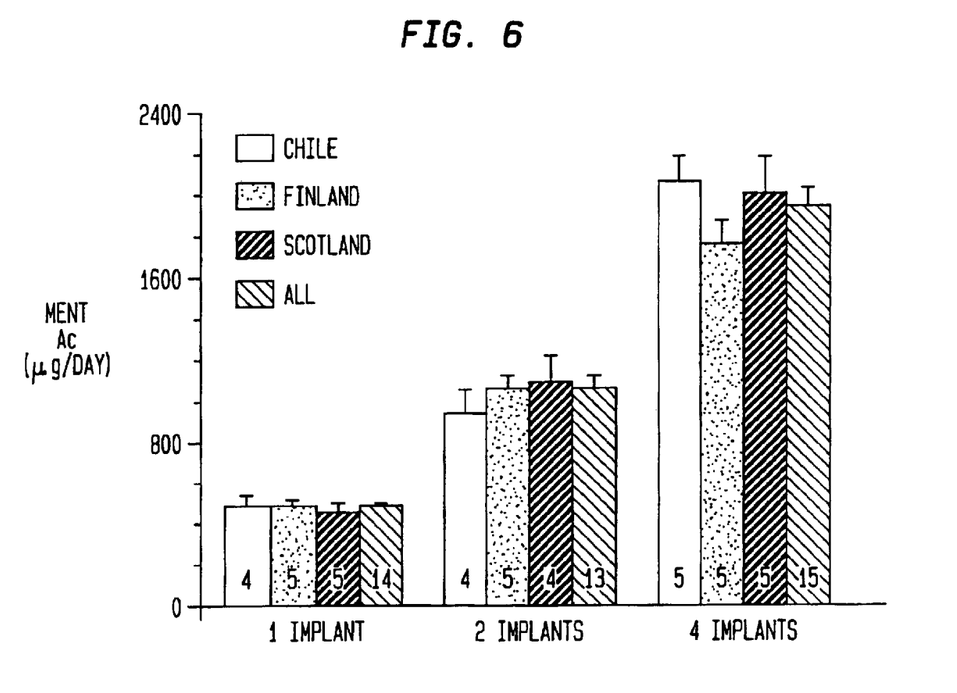
FIG. 6—is a graph of the "average" daily in vivo release of MENT Ac from either one, two or four MENT Ac implants recovered from subjects. Values are means ±SE. Number shown in each bar graph indicates sample size.

Using MENT Ac as a more specific example, an implantable rod, as described in the examples, which is capable of releasing about 500 micrograms of MENT Ac over about 24 hours, and which contains sufficient MENT Ac to provide about 500 micrograms of MENT each day for about 28 days, (see FIG. 6) can produce daily blood levels of LH which average below about 2 IU/L, levels of FSH which average just above about 2 IU/L and levels of testosterone of about 5.0 nmol/liter. See FIGS. 2–4 which respectively show the blood levels of LH, FSH and testosterone resulting from the administration of various daily amounts of MENT Ac. The "open squares" connected by a line represent the blood levels resulting from the use of a single implant as described above. As shown in FIG. 1, serum levels of MENT of between 1.0 and 2.0 nmol/L also resulted from the use of a single implant. The use of two such implants simultaneously, (FIGS. 2–4 and the "closed circles" connected by a line) or the use of a single implant which could introduce about 1,000 micrograms of MENT Ac into a subject's blood each day as described can produce daily blood levels of LH which average less than 0.5 IU/L, levels of FSH which average just above less than 0.5 IU/L and levels of testosterone of about 1.0 nmol/liter. Serum levels of MENT were, on average, between about 2.0 and about 2.5 nmol/L. See FIG. 1.

Figure 2:
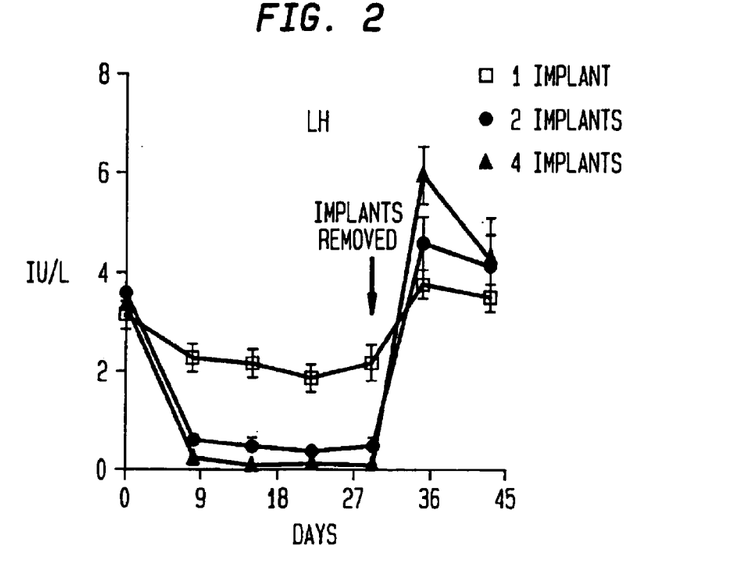
FIG. 2—is a graph of the effect of MENT Ac implants on serum levels of LH. Values shown are means ±SE.
Figure 3:
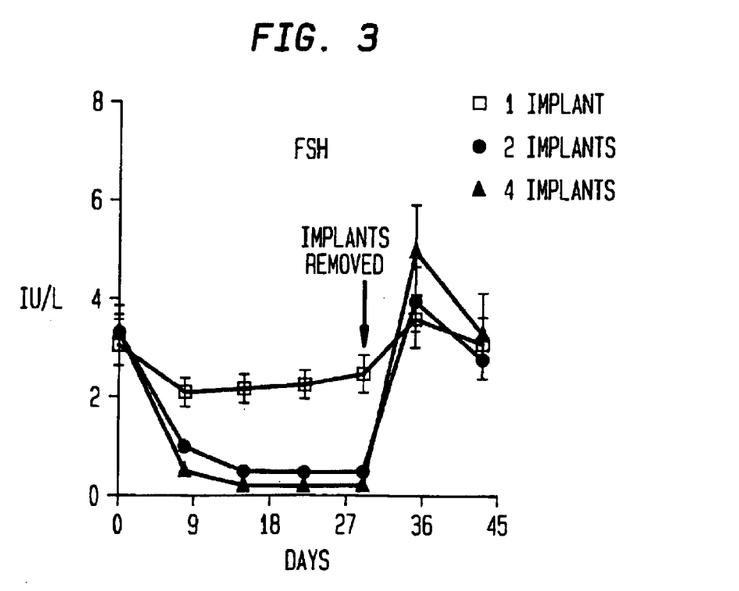
FIG. 3—is a graph of the effect of MENT Ac implants on serum levels of FSH. Values shown are means ±SE.
Figure 4:
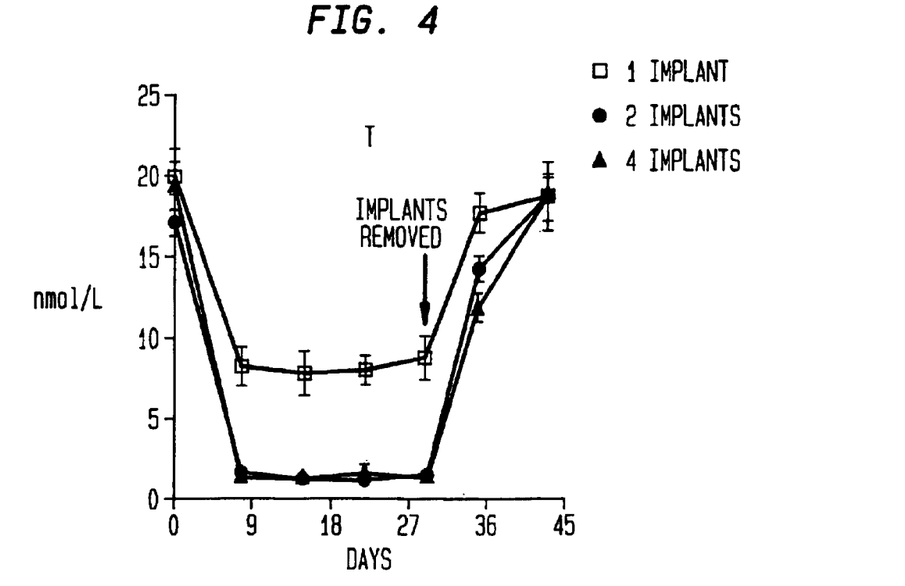
FIG. 4—is a graph of the effect of MENT Ac implants on serum levels of T. Values shown are means ±SE.

As demonstrated in FIGS. 2–4, the use of additional MENT Ac from implanted, continuous release rods, over 1000 micrograms per day, did not result in significantly lower levels of LH, FSH or testosterone. The simultaneous use of four 500 microgram per day implants resulted in levels of LH, FSH and testosterone which were very comparable to those obtained at the 1000 microgram per day level. That means that for MENT/MENT Ac, the amount of androgen which should be administered to a subject each day for the entire length of treatment should vary from between about 200 to about 2000 micrograms. More preferably, the amount of MENT administered each day will range from between about 400 and about 1500 micrograms and even more preferably, the amount of MENT administered each day will range from between about 500 to about 1000 micrograms per day.

As Example 2 demonstrates, the rate of administration may also be important in determining the amount of androgen which needs to be administered. An implant can administer 1000 micrograms of MENT Ac at roughly a constant rate over the course of 24 hours each day. However, when an equal dose of MENT, 1 mg, was administered by i.m. injection, the results, at least in terms of testosterone, were inadequate for contraceptive purposes. While the full 1 mg would make it to the blood stream, additional MENT was necessary to ensure that throughout a 24 hour period, the steady state blood levels are maintained sufficiently high, i.e.

at a constant serum level comparable to that obtained by dosing the same amount using an implant.

Figure 9:
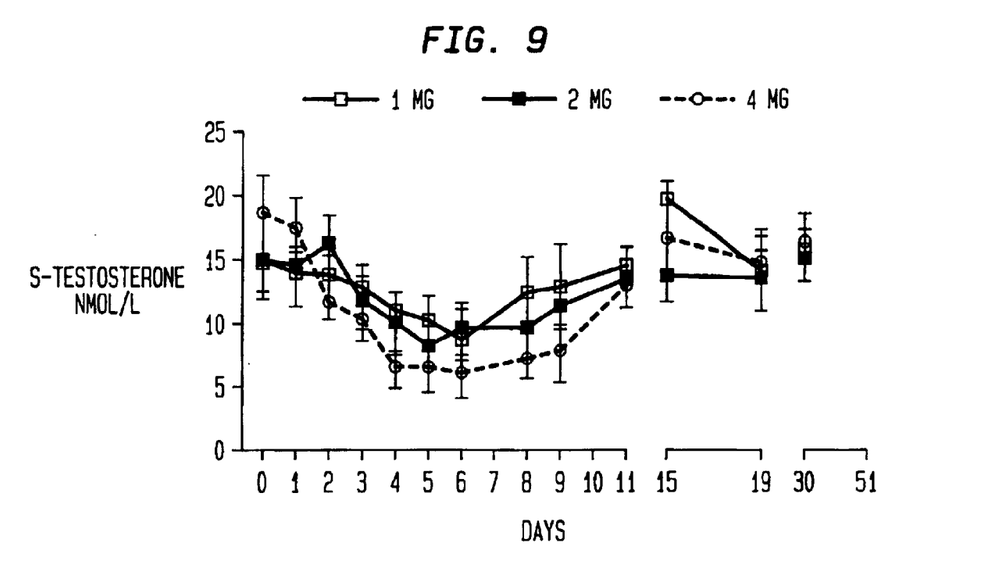
FIG. 9—is a graph of the effect of MENT by intramuscular injection (im) on serum levels of T, in a first multi-dose study. Values shown are means ±SE.
Figure 12:
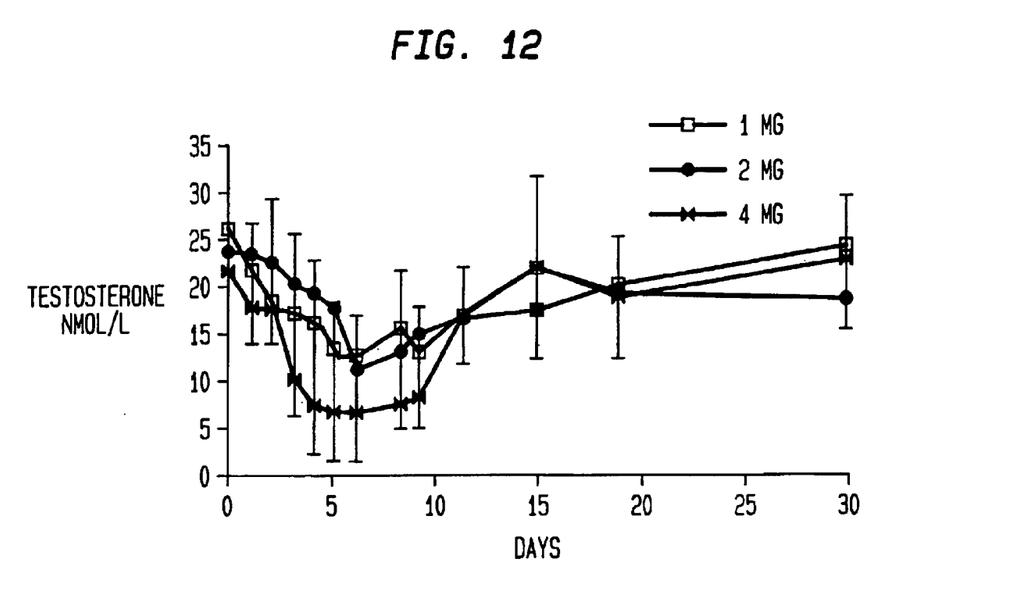
FIG. 12—is a graph of the effect of MENT by intramuscular injection on serum levels of T in a second multi-dose study. Values shown are means ±SE.

As shown in FIGS. 9 and 12, for example, the use of 4 mg of MENT by once-a-day, i.m. injection is sufficient to ensure that some level of effective contraception is obtained. Without wishing to be bound by any particular theory, it is believed that at that level, for example, blood levels of MENT remain sufficiently high throughout the day to provide effective contraception roughly equivalent to that which is obtained by the use of 500 microgram MENT Ac implants as illustrated in FIGS. 2 through 4. Therefore, the term "bioavailable amount" as used herein means an amount sufficient so as to provide minimum steady state blood levels of LH, FSH, and testosterone falling within the levels discussed herein and effective to provide contraception. The amount of drug provided in a once-a-day, non-sustained release system may need to be significantly higher than needed for constant release dosage forms to provide comparable minimum steady state drug levels comparable to that obtainable by an implant or other long-term constant release systems in accordance with the present invention throughout a 24 hour day cycle.

The amounts of other androgens necessary to provide the desired blood levels of LH, FSH and testosterone will vary as previously described. However, the amounts can be simply determined by administering a fixed amount of an androgen and measuring the resulting blood levels of LH, FSH and testosterone using conventional, commercially known techniques. Once the blood levels of these compounds have been determined, the amount of androgen administered can be adjusted accordingly, either higher or lower, to provide the desired blood levels of LH, FSH and testosterone.

LH, FSH and testosterone are more than mere markers indicating something about the behavior and bioavailability of the androgen. They are each important in sperm production. LH stimulates Lydig cells to release testosterone. Testosterone is important for spermatogenesis. FSH stimulates germ cells. If germ cells are present, but insufficient testosterone is available, spermatogenesis is depressed. The reverse is also true. In accordance with the present invention, sperm production is compromised in two ways. Since FSH is reduced, so too are germ cells. Moreover, the reduction is LH and testosterone inhibits spermatogenesis. Yet, sexual function is maintained and potential side effects reduced or eliminated.

This underscores the importance of using androgens other than testosterone. The use of testosterone is actually counterproductive as it elevates blood testosterone levels and may help support spermatogenesis of any available germ cells.

The methods of the present invention can be practiced using conventional dosage forms and techniques. First, one must select the type of therapy desired, either contraception or non-contraceptive androgen replacement. To a large degree, the objective, the physical condition of the patient, and the dosage form will dictate the amount of androgen. Generally, more androgen is needed for contraceptive methods, less for non-contraceptive androgen replacement. The androgen selected will also be important in determining the dose as will the route of administration. Once the objective, the androgen and the desired route are selected, the androgen can be administered in conventional formulations and blood tests can be given to confirm the resulting blood levels of androgen, LH, FSH and testosterone. If the levels need to be adjusted, then the amount of androgen can be changed, another androgen can be selected or another dosage form can be employed.

For example, if a subject is to be given 500 micrograms of MENT per day via a once-a-day transdermal patch, a new patch must be provided and applied to the skin of the subject at about the same time each day. The patch may contain an excess of MENT. But the amount that is bioavailable is 500 micrograms. There may also be an initial burst of androgen when the patch is first applied, but the rate of delivery will adjust to a more constant rate and the average amount which is bioavailable should fall within the ranges described. If the steady state blood levels are, on average over the day, too low, i.e., the blood levels of LH and FSH are above 2.5 IU/L and the level of testosterone is above 10 nmol/liter, (or above some lower level as described depending on the needs of the subject and the objective of the doctor), several options are open. Subsequent doses administered by a transdermal patch can be increased, the dosage form can be changed to, for example, a subcutaneous implant and/or a more potent androgen, one which is compatible with the pharmaceutical carrier and preferably non-5α-reducible, can be used. What is important is the long term maintenance of blood levels of LH, FSH and testosterone below certain limits. Therefore, when using MENT transdermal patches for that purpose, what is important is that minimum steady state blood levels of the androgen be comparable to those which result from the use of MENT or MENT Ac containing subdermal implants as discussed herein and as described in the examples.

Dosage forms which contain a sufficient quantity of the correct androgen are also contemplated. These dosage forms, unlike those that have gone before, will provide sufficient androgen to be contraceptively effective without significant side effects. The dosage forms contemplated include, without limitation, the androgen and a pharmaceutically acceptable carrier.

Pharmaceutically acceptable carriers, in the case of the present invention, can include, without limitation, chemical formulations such as creams, salves, lotions, liquids, gels injectable liquids, liquids capable of IV or IP administration, capsules and/or tablets capable of delivering androgen over an immediate period or over an extended period of hours or days, as well as devices such as transdermal patches, pumps and implants. Pumps and implants can be subcutaneous or implantable elsewhere and can include both errodable and diffusion-based devices, as well as any other functionally equivalent devices known in the art. These can all be made and administered in accordance with procedures well known in the industry.

Intravenous or injectable dosage forms can be comprised of any suitable liquid carrier which can dissolve or sufficiently emulsify the androgen to allow for safe administration. Often these formulations can also include viscosity modifiers, surfactants, preservatives solubilizing agents, diluents and additives useful for rendering the solutions isotonic. Other drugs or pharmaceuticals can also be administered along with the androgen from the same dosage form.

Topical dosage forms can include androgen formulated in a lotion, cream, salve, paste or gel. Any such topical vehicle known in the art may be used so long as it is capable of administering a suitable quantity of androgen in accordance with the present invention. Often these formulations can also include viscosity modifiers, surfactants, preservatives, solubilizing agents, diluents, permeation enhancers, colors, fragrances and skin care additives like conditioners and humectants. Other drugs or pharmaceuticals can also be administered along with the androgen from the same dosage form. These topical formulations can include buccal dosage forms as well.

In accordance with the present invention, androgen can also be administered through oral dosage forms such as liquids, oral suspensions, elixirs, syrups, capsules, caplets or tablets. Any formulation which can administer the dosage form orally is contemplated including immediate release and sustained release dosage forms. Often these formulations can also include viscosity modifiers, surfactants, preservatives solubilizing agents, microcapsules, microparticles, granules, diluents, binders, fillers, lubricants, colors, flavors and the like. Other drugs or pharmaceuticals can also be administered along with the androgen from the same dosage form.

Finally, in a preferred aspect of the present invention, an implant or pump may be used. Implants include implantable subcutaneous devices such as those disclosed in U.S. Pat. No. 5,733,565, the text of which is hereby incorporated by reference. However, in accordance with the present invention, the implant (or implants) are designed to provide sufficient androgen to provide contraception. Therefore, when MENT Ac is used, for example, the implants will be capable of providing at least about 500 micrograms per day, each day for at least 30 days and preferably about 180 days. Preferably, the amount of MENT Ac administered each day would not be greater than about 2000 micrograms per day and more preferably no more than 1000 micrograms. If MENT Ac were used in androgen replacement implants where contraception was not desired, these same implants would generally provide less than about 500 micrograms of MENT each day. While implants of this type are preferred, any similar devices designed to remain in the body and administer, in as nearly a uniform manner as possible, an amount of, in this case, an androgen as described herein may be used. These implants can be produced and administered as known in the art. It should be noted that MENT Ac is readily hydrolyzed to MENT and it has been found that MENT Ac is superior in terms of bioavailability in certain subcutaneous implants as discussed in the examples. MENT may be preferred in other implants and MENT is preferred for transdermal dosage forms.

It will be appreciated that techniques for the administration of various drugs, including such structurally similar compounds as steroids, are well known in the art. Therefore, it is unnecessary to describe in detail administration details for oral, topical, IV and implantation techniques. Any conventional technique or dosage form is suitable provided that it can reliably administer the correct amount of the androgens in question. Knowing the objective (contraception or non-contraceptive androgen replacement), the types of androgens useful in accordance with the present invention, the blood levels of various compounds desired consistent with that objective and methods of determining the blood levels of important compounds as indicated will allow for one to practice the invention with any dosage form or dosing technique.

EXAMPLE 1

Forty-five healthy, normal male subjects were selected for a study of the contraceptive effect of androgens alone. Subjects were treated over the course of four weeks, during which extensive blood work-ups were undertaken. The subjects were divided into three groups of 15 each. Group A received one subcutaneous implant, Group B received two subcutaneous implants and Group C received four subcutaneous implants. Implants remained in place for 28 consecutive days. The implants were manufactured by the Center for Biomedical Research and the Population Council of New York, 1230 York Avenue, New York, N.Y. 10021 and each implant had a length of 4.4 cm, a drug load per implant of 112±4 mg of MENT Ac and a release rate of approximately 500 micrograms per implant per day, based on an in vivo study.

The procedure for production of the implants involved three basic steps. In brief, cores were prepared containing 60% w/w of MENT Ac and 40% w/w of Ethylene Vinyl Acetate copolymer (EVA); 25% w/w of VA content. The cores were then encased in EVA (9% VA content) and the ends of the tubing were sealed with melted EVA (25% VA content).

A. Preparation of Cores Containing 60% of MENT Ac 1.5 g of EVA pellets (25% VA) was weighed into 18 ml of methylene chloride and dissolved overnight. 2.225 g of MENT Ac was weighed and added to the solution of EVA in methylene chloride and Vortexed for 3 minutes to mix. The methylene chloride was evaporated under vacuum, at room temperature, for 2 hours. 2.3 g of the resulting solid dispersion was obtained. This solid dispersion was filled into a stainless steel syringe and heated to 120° C. for 5 minutes using the thermostatically controlled heating jacket for the syringe. The solid dispersion was then extruded by pressing the syringe, using the small laboratory press, into a brass mold with grooves of 2.38 mm diameter and 4.5 cm length. The mold was opened and the cores cut into 4 cm pieces. The cores were weighed individually and any core deviating from the mean weight by ±7.5% were discarded. Cores were taken at random and tested for MENT Ac content using known methods. The mean value must not differ from the expected values by more than ±7.5% and none of the individual values may differ from the mean by more than 10%.

B. Encasement of the Core Rods by EVA Tubing

EVA (9% VA) tubing (about 2.55 mm in diameter) was cut into 5 cm lengths and soaked in methylene chloride for about 1–3 minutes. Each of the 4 cm core rods was introduced into one of the soaked 5 cm pieces of EVA tubing leaving about 0.5 cm empty on both ends and left overnight to get rid of any residual methylene chloride.

C. Sealing of the Two Ends of the Filled Tubing

About 2 g of EVA (25% VA) was heated in the stainless steel syringe equipped with the thermostatically controlled heating jacket for 5 minutes at 120° C. The melted EVA was then injected into both ends of each filled tubing. The implants were heat sealed at 70° C. for 10 minutes to enhance the adherence between the inside core and the outside tubing and to ensure complete removal of any residual methylene chloride.

The total duration of the study was 42 days. Each man included in the study was assessed through a medical history and a complete general physical examination and a determination of general eligibility. Subjects were tested on a weekly basis for six consecutive weeks at approximately the same time each day. Day 1 was the date of the subdermal implant's insertion and Day 29 was removal. On the last day of the study, Day 43, subjects received a general physical examination, as well as an additional battery of blood tests. Blood samples for hormone immuno assays MENT (7 mL), FSH, LH and testosterone (5 mL for the last 3 hormones together) were obtained during pre-admission and each subsequent visit.

FIG. 2 illustrates the effect of MENT Ac implants on mean serum LH concentration. By the first post implant visit on day 8, levels of LH had already dropped significantly. In fact, subjects to whom 2 or 4 implants (500 micrograms each) were administered had nearly undetectable levels of LH. By suppressing LH, testosterone production is suppressed. This is demonstrated in FIG. 4 which illustrates the effect of MENT Ac implants on the mean serum T concentration (testosterone). Again, subjects to whom two or four implants had been administered exhibited very low testosterone levels. Subjects who received a single implant still showed much reduced levels of testosterone. A reduction in testosterone reduces or eliminates spermatogenesis. However, because androgen is being supplied, sexual function is generally maintained.

Finally, FIG. 3 illustrates the effect of MENT Ac implants on the mean serum FSH concentration. The use of the androgen containing implants had a significant impact on the serum FSH concentration in subjects. FSH stimulates germ cell production. If germ cells are present, but testosterone is insufficient, then spermatogenesis cannot take place and sperm cells will not be produced. Similarly, if FSH concentrations are low enough, germ cells will not be produced and spermatogenesis cannot take place irrespective of testosterone levels. Without wishing to be bound by any theory of operation, by the use of androgen, in accordance with the present invention, sperm production can be controlled by effectively reducing both effective testosterone levels and germ cell production.

EXAMPLE 2

Two multiple injection studies were undertaken in which groups of four normal, non-sterile men each received 1, 2 or 4 mg of MENT daily by intramuscular (i.m.) injection for six consecutive days (24 men, 12 in each study). The formulation in each injection included the appropriate amount of MENT suspended in 27.6 mg/mL of polyethylene glycol, 1.8 mg/mL of Tween 80 and 8.3 mg/mL of sodium chloride. Serum FSH, LH and testosterone levels were measured daily. The results are illustrated in FIGS. 7–12.

Figure 7:
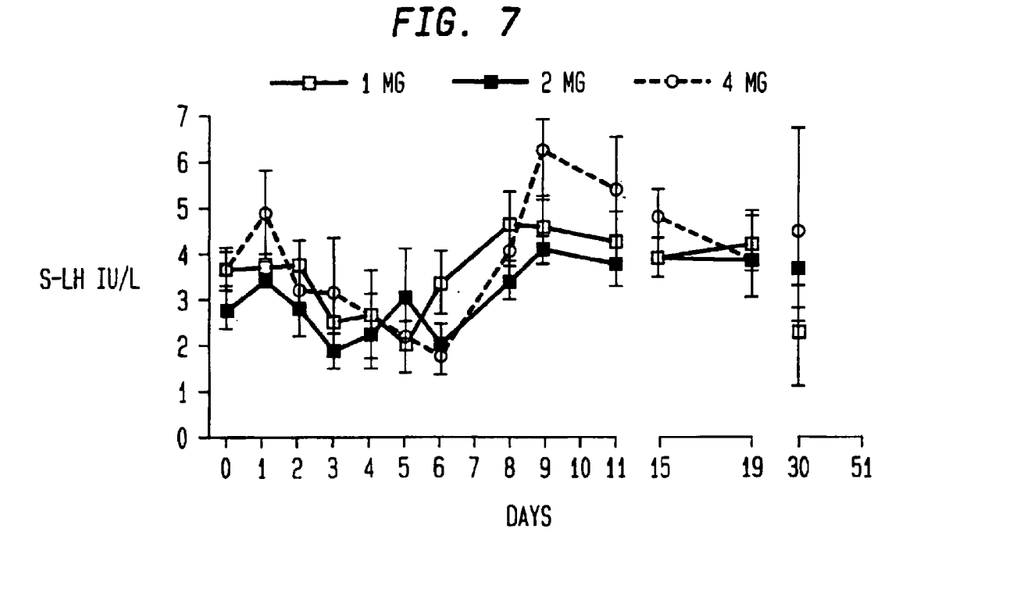
FIG. 7—is a graph of the effect of MENT by intramuscular injection (im) on serum levels of LH in a first multi-dose study. Values shown are means ±SE.
Figure 8:
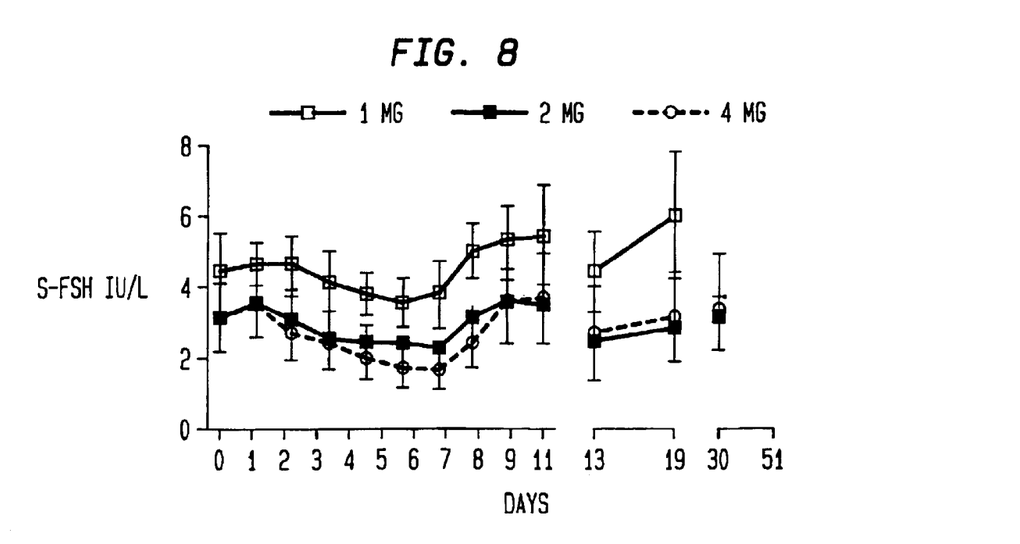
FIG. 8—is a graph of the effect of MENT by intramuscular injection (im) on serum levels of FSH in a first multi-dose study. Values shown are means ±SE.
Figure 10:
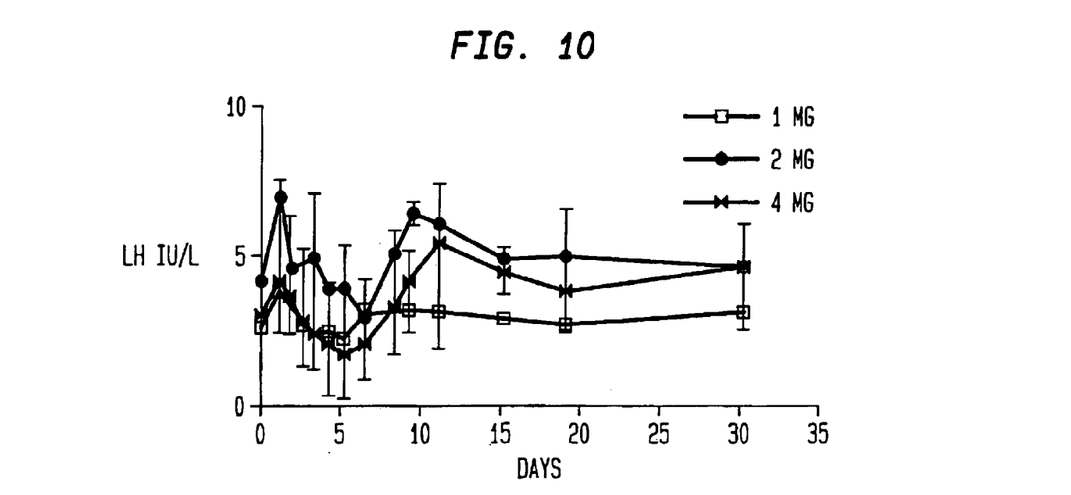
FIG. 10—is a graph of the effect of MENT by intramuscular injection on serum levels of LH in a second multi-dose study. Values shown are means ±SE.
Figure 11:
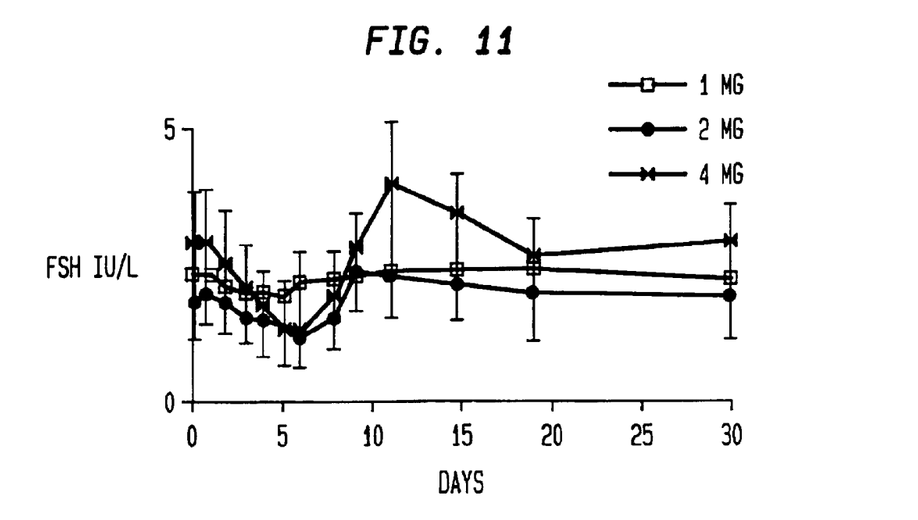
FIG. 11—is a graph of the effect of MENT by intramuscular injection on serum levels of FSH in a second multi-dose study. Values shown are means ±SE.

In both studies, all three doses of MENT caused a gradual decrease in serum gonadotropins and testosterone levels which reached their lowest levels by the end of treatment at six days. The values returned to the normal range by day 15–30 of the study period. With reference to FIG. 8 (open boxes connected by a line=1 mg, closed boxes connected by a line=2 mg, open circles connected by a line=4 mg) a dose of at least 4 mg was required to obtain serum levels of FSH below two international units ("IU") per liter by day 6. This must be compared with the results obtained by the use of 1000 µg (1 mg) of the same androgen delivered by a subcutaneous implant as illustrated in FIGS. 2–4 and Example 1. Therefore, considerably more of this same androgen was required to obtain certain depressed serum levels of LH, FSH and testosterone in males when the androgen was administered through a once-a-day intramuscular injection when compared to continuous release implants. Indeed, depending upon the level of LH, FSH and testosterone desirable by a particular health care professional, a dose significantly in excess of 4 mg may be necessary for this type of dosage form. FIG. 7 illustrates the level of serum LH achieved in the first study and FIG. 9 illustrates the level of serum testosterone achieved. FIGS. 10–12 illustrate the levels of LH, FSH and testosterone realized by the same protocol at the second testing site. Both the data and the overall trends of both studies are largely the same.

What is claimed is:

1. A method of male contraception comprising the step of: administering to a non-sterile male subject a predetermined amount of a non-5α-reducible androgen which is sufficient to render said male subject reversibly sterile for a predetermined period of time and which provides said male subject with blood levels of LH and FSH of 2.5 IU/L or less and testosterone of 10 nmol/liter or less and wherein said androgen is substantially the only sterilizing agent administered to said male subject for the purposes of contraception.

2. A method of male contraception consisting essentially of the step of:
administering to a non-sterile male subject a predetermined amount of a non-5α-reducible androgen which is sufficient to render said male subject reversibly sterile for a predetermined period of time.

3. The method of claim 1 or 2 wherein said androgen is MENT and its pharmaceutically acceptable salts.

4. The method of claim 3 wherein said predetermined period of time is at least 1 day and said predetermined amount of MENT and pharmaceutically acceptable salts thereof is an amount which is sufficient to render said male subject reversibly sterile each day over said predetermined period.

5. The method of claim 4 wherein said predetermined period of time is a plurality of days and said predetermined amount of MENT and pharmaceutically acceptable salts thereof is an amount which is sufficient to render said male subject reversibly sterile each day over said predetermined period.

6. The method of claim 5 wherein said predetermined period of time is at least 7 days and said predetermined amount of MENT and pharmaceutically acceptable salts thereof is an amount which is sufficient to render said male subject reversibly sterile each day over said predetermined period.

7. The method of claim 5 wherein said predetermined period of time is at least 30 days and said predetermined amount of MENT and pharmaceutically acceptable salts thereof is an amount which is sufficient to render said male subject reversibly sterile each day over said predetermined period.

8. The method of claim 5 wherein said predetermined period of time is at least 180 days and said predetermined amount of MENT and pharmaceutically acceptable salts thereof is an amount which is sufficient to render said male subject reversibly sterile each day over said predetermined period.

9. The method of claim 3 wherein said predetermined amount of MENT or a pharmaceutically acceptable salt thereof, is a bioavailable amount ranging from between about 200 to about 2000 micrograms/day.

10. The method of claim 9 wherein said predetermined amount of MENT or a pharmaceutically acceptable salt thereof, is a bioavailable amount ranging from between about 400 to about 1500 micrograms/day.

11. The method of claim 10, wherein said predetermined amount of MENT or a pharmaceutically acceptable salt thereof, is a bioavailable amount ranging from between about 500 to about 1000 micrograms/day.

12. The method of claim 11 wherein said predetermined amount of MENT or a pharmaceutically acceptable salt thereof, is a bioavailable amount providing mean steady state serum levels of 1.0 nmol/Liter/day or greater.

13. The method of claim 1 wherein said predetermined amount of a non-5α-reducible androgen is sufficient to provide said male subject with blood levels of LH and FSH of 2.0 IU/L or less and testosterone of 5 nmol/liter or less.

14. The method of claim 13 wherein said predetermined amount of a non-5α-reducible androgen is sufficient to provide said male subject with blood levels of LH and FSH of 1.5 IU/L or less and testosterone of 4 nmol/liter or less.

15. The method of claim 14 wherein said predetermined amount of a non-5α-reducible androgen is sufficient to provide said male subject with blood levels of LH and FSH of 1.0 IU/L or less and testosterone of 3 nmol/liter or less.

16. The method of claim 1 or 2 wherein said predetermined amount of a non-5α-reducible androgen is administered to said subject by injection.

17. The method of claims 1 or 2 wherein said predetermined amount of a non-5α-reducible androgen is administered to said subject by implant.

18. The method of claim 1 or 2 wherein said predetermined amount of a non-5α-reducible androgen is administered to said subject by topical application.

19. The method of claim 14 wherein said predetermined amount of a non-5α-reducible androgen is administered to said subject as a cream, lotion, gel or in a transdermal patch.

20. The method of claim 1 or 2 wherein said predetermined amount of androgen is administered to said subject orally.

* * * * *